United States Patent

Harada et al.

[11] Patent Number: 5,994,553
[45] Date of Patent: Nov. 30, 1999

[54] METHOD FOR PREPARING 2-MERCAPTOTHIAZOLE

[75] Inventors: Katsumasa Harada; Akio Matsushita; Taku Nakamura; Katsuhiko Mizutare; Takafumi Hirakawa; Ken Ikuno; Noriaki Iwase, all of Ube, Japan

[73] Assignee: Ube Industries, Ltd., Yamaguchi, Japan

[21] Appl. No.: 09/211,446

[22] Filed: Dec. 15, 1998

[30] Foreign Application Priority Data

Dec. 26, 1997 [JP] Japan ................................ 9-359791

[51] Int. Cl.$^6$ ................................................. C07D 277/36
[52] U.S. Cl. ............................................................ 548/182
[58] Field of Search ............................................. 548/182

[56] References Cited

U.S. PATENT DOCUMENTS 2,426,397 8/1947 Jones .

FOREIGN PATENT DOCUMENTS

WO 98 37074 8/1998 WIPO .

OTHER PUBLICATIONS

Chemical Abstracts 59:6380a (Kolosova), 1963.
Chemical Abstracts, vol. 59, No. 6, Sep. 16, 1963, Kolosova: "2–Mercaptothiazole", col. 6380a, XP–002096152 of Zh. Prikl. Khim. 36(4), 931–932 (1963).

Chanon et al.: "Étude de la réaction de cyclisation . . . ", Bull. Soc. Chim. FR., 1968 pp. 2863–2868, XP–002096150.

Bastianelli et al.: "Synthèses dans la série des alcoylthio–2–thiazoles", Bull. Soc. Chim. FR., 1967, pp. 1948–1951, XP–002096151.

Mathes R. A. et al: "A Synthesis of 2–Thiazolethiol and its Disulfide", Journal of the American Chemical Society, vol. 70, No. 4, Apr. 1948, pp. 1451–1452 XP–002065288.

Zh. Prikl. Khim. 36(4) 931–2 (1963) by M.O. Kolosova.

*Primary Examiner*—Robert Gerstl
*Attorney, Agent, or Firm*—Frishauf, Holtz, Goodman, Langer & Chick, P.C.

[57] ABSTRACT

Disclosed is a method for preparing 2-mercaptothiazole, which comprises adding a dithiocarbamate salt represented by the formula (1):

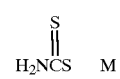

(1)

wherein M is a cation, to a chloroacetaldehyde solution in the presence of an acid.

18 Claims, No Drawings

METHOD FOR PREPARING 2-MERCAPTOTHIAZOLE

BACKGROUND OF THE INVENTION

1. Field of the Invention

The present invention relates to 2-mercaptothiazole which is useful as an intermediate of medicines and agricultural chemicals.

2. Prior Art

As a conventional method for preparing 2-mercaptothiazole by reacting a dithiocarbamate salt with chloroacetaldehyde, there are described methods in literatures (1) Bull. Soc. Chim. Fr., 1948 (1967) and (2) Bull. Soc. Chim. Fr., 2863 (1968). In literature (1), 2-mercaptothiazole can be prepared with the yield of 55% by adding a chloroacetaldehyde solution to a dithiocarbamate salt solution. In literature (2), 2-mercaptothiazole can be prepared with the yield of 70% by adding chloroacetaldehyde and ammonium dithiocarbamate to an acidic dithiocarbamate salt solution at the same time.

However, either of these methods is an industrially unsatisfied method for preparing 2-mercaptothiazole, since they result in the low yield of 2-mercaptothiazole and in addition thereto a polymeric product separation of which is difficult is by-produced in the reaction system.

SUMMARY OF THE INVENTION

An object of the present invention is to provide a new method for preparing 2-mercaptothiazole which is useful as an intermediate of medicines and agricultural chemicals, while restricting the occurrence of by-product, with a high yield.

For the purpose of solving the problems involved in the prior art, the present inventors have investigated about a new method for preparing 2-mercaptothiazole and as a result, they have accomplished the present invention.

The present invention relates to a method for preparing 2-mercaptothiazole, which comprises adding a dithiocarbamate salt represented by the formula (1):

(1)

wherein M is a cation, to a chloroacetaldehyde solution in the presence of an acid.

DESCRIPTION OF THE PREFERRED EMBODIMENTS

The present invention will be explained in detail in the following.

A solvent employable for preparing a chloroacetaldehyde solution is not limited as long as it does not participate in the reaction. Water, an organic solvent such as methanol, ethanol, propanol, acetonitrile and tetrahydrofuran, and the mixture thereof can be employed. From the view point of making it easy to isolate the objective compound, water is preferably used.

As a solution of chloroacetaldehyde dissolved in water, the solution which is commercially available can be employed.

An acid employable for acidifying a chloroacetaldehyde solution includes hydrogen chloride, sulfuric acid, hydrogen bromide, phosphoric acid, nitric acid, p-toluenesulfonic acid and the mixture thereof. Hydrogen chloride and sulfuric acid are preferred.

Hydrogen chloride and hydrogen bromide can be employed in the form of a gas and also in the form of its aqueous solution.

The amount of an acid to be employed is preferably 0.8–5.0 mol, more preferably 0.9–2.5 mol, based on 1 mol of chloroacetaldehyde.

The addition of an acid to the chloroacetaldehyde solution can be carried out by adding the above acid to the chloroacetaldehyde solution, by adding the chloroacetaldehyde solution to a solution of the acid, or by suitably adding the above acid while adding a dithiocarbamate salt represented by the formula (1) to the chloroacetaldehyde solution. Incidentally, it is preferred that the acid solution is the mixture of the above acid and a solvent employed in the preparation of the above chloroacetaldehyde solution; and water can be employed as the solvent from the view point of making it easy to isolate the objective compound.

A cation of a dithiocarbamate salt includes ammonium and an alkali metal, preferably ammonium. The dithiocarbamate salt can be added to an acidic chloroacetaldehyde solution in the form of a solid or a solution. A solvent employable for preparing the dithiocarbamate salt solution includes a lower alcohol such as methanol, ethanol, propanol and butanol, water, and the mixture thereof etc., and preferably water.

In the preparation of the dithiocarbamate salt solution, the amount of a solvent to a dithiocarbamate salt is not limited as long as the dithiocarbamate salt is dissolved in the solvent, and may be 1–60% by weight, preferably 3–55% by weight, based on total weight of the solvent used and the dithiocarbamate salt. From the view point of productivity, it is better that the amount of the solvent is as little as possible, and 30–55% by weight. The temperature, at which the dithiocarbamate salt is added to the chloroacetaldehyde solution in the presence of the acid, is preferably 0° C.–about 50° C., more preferably about 20–about 35° C. The molar ratio of the dithiocarbamate salt to chloroacetaldehyde to be employed is preferably 0.7–5.0, more preferably 0.9–3.0 from the view point of economicity.

2-mercaptothiazole can be prepared by further continuing the reaction of the above mixed solution at the same temperature (20–35° C.). However, from the view point of shortening the time of production and heightening the yield, the reaction temperature is preferably about 40–about 90° C., more preferably 50–80° C. Incidentally, although the reaction temperature may not be raised when an excess amount of dithiocarbamic acid is employed because carbon disulfide occurs by the decomposition due to an acid, the reaction temperature can be raised by carrying out the reaction while removing carbon disulfide outside the system by distillation. The reaction time for preparing 2-mercaptothiazole is usually 2–10 hours after the addition of the dithiocarbamate salt. A method for isolating and purifying the produced 2-mercaptothiazole from the reaction system is not limited. For example, when an organic solvent such as alcohol, acetonitrile and tetrahydrofuran is employed as a solvent, it can be adopted to extract itself with a solvent insoluble to water or to remove the organic solvent in a step followed by extracting the aqueous mixture with a solvent insoluble to water; and when such an organic solvent is not employed, it can be adopted to extract directly with a solvent insoluble to water. After the concentration, further purification may be made by column purification or recrystallization method.

Incidentally, in case of the present invention, it has been confirmed by NMR or elemental analysis that there is a possibility that a precursor other than 2-mercapto-4-hydroxythiazoline occurs.

EXAMPLES

In the following, the present invention will be explained concretely while referring to Examples and Comparative examples. Incidentally, the scope of the present invention is not limited by these Examples.

Example 1

10.14 g (100 mmol) of a concentrated hydrochloric acid was added to 17.44 g (100 mmol) of an aqueous chloroacetaldehyde solution (45% by weight) at the room temperature. Further, an aqueous solution of 12.12 g (110 mmol) of ammonium dithiocarbamate dissolved in 12.12 g of water was add dropwise to the mixture under cooling by a water bath at the room temperature over 50 minutes. After completion of the dropwise addition, the mixture was stirred at the same temperature further for 60 minutes. After completion of the stirring, the reaction temperature of the mixture was raised to 74° C. followed by stirring at the same temperature for 2.5 hours while heating. Then, it was cooled to the room temperature and extracted with 50 ml of ethyl acetate three times. After drying over anhydrous magnesium sulfate, it was concentrated followed by quantifying the obtained solid by liquid chromatography.

amount: 10.58 g
purity: 98.4%
yield: 88.8%

Example 2

The same procedure as in Example 1 was carried out, except that the amount of ammonium dithiocarbamate to be employed was changed to 11.02 g (100 mmol) and the amount of water for dissolving ammonium dithiocarbamate was changed to 11.02 g, followed by the quantification by liquid chromatography.

amount: 9.58 g
purity: 95.7%
yield: 78.2%

Example 3

8.11 g (80 mmol) of a concentrated hydrochloric acid was added to 13.96 g (80 mmol) of an aqueous chloroacetaldehyde solution (45% by weight) at the room temperature. Further, an aqueous solution of 13.22 g (120 mmol) of ammonium dithiocarbamate dissolved in 13.22 g of water was added dropwise to the mixture under cooling a water bath at the room temperature over 50 minutes. After completion of the dropwise addition, it was further stirred at the same temperature. After completion of the stirring, the reaction temperature of the mixture was raised to 74° C. to complete the reaction. Then, it was cooled to the room temperature and extracted with 50 ml of ethyl acetate three times. After drying over anhydrous magnesium sulfate, it was concentrated followed by quantifying the obtained solid by liquid chromatography.

amount: 8.86 g
purity: 91.9%
yield: 86.9%

Example 4

15.21 g (150 mmol) of a concentrated hydrochloric acid was added to 17.44 g (100 mmol) of an aqueous chloroacetaldehyde solution (45% by weight) at the room temperature. Further, an aqueous solution of 12.12 g (110 mmol) of ammonium dithiocarbamate dissolved in 12.12 g of water was added dropwise to the mixture under cooling a water bath at the room temperature over 50 minutes. After completion of the dropwise addition, it was further stirred at the same temperature. After completion of the stirring, the reaction temperature of the mixture was raised to 74° C. to complete the reaction. Then, it was cooled to the room temperature and extracted with 50 ml of ethyl acetate three times. After drying over anhydrous magnesium sulfate, it was concentrated followed by quantifying the obtained solid by liquid chromatography.

amount: 11.11 g
purity: 98.9%
yield: 93.8%

Example 5

30 ml of 2N HCl (60 mmol) was added to 10.47 g (60 mmol) of an aqueous chloroacetaldehyde solution (45% by weight) at the room temperature. Further, an aqueous solution of 9.92 g (90 mmol) of ammonium dithiocarbamate dissolved in 9.92 g of water was added dropwise to the mixture under cooling by a water bath at the room temperature over 40 minutes. After completion of the dropwise addition, it was further stirred at the same temperature for 30 minutes. After completion of the stirring, the reaction temperature of the mixture was raised to 60° C. to complete the reaction. Then, it was cooled to the room temperature and extracted with 50 ml of ethyl acetate three times. After drying over anhydrous magnesium sulfate, it was concentrated followed by quantifying the obtained solid by liquid chromatography.

amount: 6.31 g
purity: 88.5%
yield: 79.4%

Example 6

10 ml of 6N HCl (60 mmol) was added to 10.47 g (60 mmol) of an aqueous chloroacetaldehyde solution (45% by weight) at the room temperature. Further, an aqueous solution of 9.92 g (90 mmol) of ammonium dithiocarbamate dissolved in 9.92 g of water was added dropwise to the mixture under cooling by a water bath at the room temperature over 45 minutes. After completion of the dropwise addition, it was further stirred at the same temperature for 30 minutes. After completion of stirring, the reaction temperature of the mixture was raised to 60° C. to complete the reaction. Then, it was cooled to the room temperature and extracted with 50 ml of ethyl acetate three times. After drying over anhydrous magnesium sulfate, it was concentrated followed by quantifying the obtained solid by liquid chromatography.

amount: 6.24 g
purity: 94.5%
yield: 83.8%

Example 7

10.14 g (100 mmol) of a concentrated hydrochloric acid was added to 17.44 g (100 mmol) of an aqueous chloroacetaldehyde solution (45% by weight) at the room temperature. After cooling the mixture to 0° C., an aqueous solution of 12.12 g (110 mmol) of ammonium dithiocarbamate dissolved in 12.12 g of water was added dropwise to the mixture under cooling by a water bath at the same temperature over 50 minutes. After completion of the dropwise addition, it was further stirred at 0° C. for 60 minutes. After completion of the stirring, the reaction temperature of the mixture was raised to 74° C. to complete the reaction. Then, it was cooled to the room temperature and extracted with 50 ml of ethyl acetate three times. After drying over anhydrous magnesium sulfate, it was concentrated followed by quantifying the obtained solid by liquid chromatography.

amount: 10.33 g
purity: 95.9%
yield: 84.5%

Example 8

24.33 g (240 mmol) of a concentrated hydrochloric acid was added to 13.96 g (80 mmol) of an aqueous chloroacetaldehyde solution (45% by weight) at the room temperature. Further, an aqueous solution of 9.70 g (88 mmol) of ammonium dithiocarbamate dissolved in 9.70 g of water was added dropwise to the mixture under cooling by a water bath at the room temperature over 50 minutes. After completion of the dropwise addition, it was further stirred at the same temperature for 60 minutes. After completion of the stirring, the reaction temperature of the mixture was raised to 75° C. followed by stirring the same temperature for 7 hours. Then, it was cooled to the room temperature and extracted with 50 ml of ethyl acetate three times. After drying over anhydrous magnesium sulfate, it was concentrated followed by quantifying the obtained solid by liquid chromatography.

amount: 7.85 g
purity: 87.7%
yield: 73.4%

Example 9

7.30 g (72 mmol) of a concentrated hydrochloric acid was added to 15.70 g (90mmol) of an aqueous chloroacetaldehyde solution (45% by weight) at the room temperature. Further, an aqueous solution of 10.91 g (99 mmol) of ammonium dithiocarbamate in 10.91 g of water was added dropwise to the mixture under cooling by a water bath at the room temperature over 50 minutes. After completion of the dropwise addition, it was further stirred at the same temperature for 60 minutes. After completion of the stirring, the reaction temperature of the mixture was raised to 75° C. to complete the reaction. Then, it was cooled to the room temperature and extracted with 50 ml of ethyl acetate three times. After drying over anhydrous magnesium sulfate, it was concentrated followed by quantifying the obtained solid by liquid chromatography.

amount: 7.29 g
purity: 91.6%
yield: 63.3%

Example 10

9.13 g (90 mmol) of a concentrated hydrochloric acid and a solution of 10.91 g (99 mmol) of ammonium dithiocarbamate dissolved in 10.91 g of water were added dropwise to 15.70 g (90 mmol) of an aqueous chloroacetaldehyde solution (45% by weight) at the room temperature over 30 minutes substantially equimolar amounts. After completion of the dropwise addition, it was further stirred at the same temperature for 60 minutes. After completion of the stirring, the reaction temperature of the mixture was raised to 75° C.

to complete the reaction. Then, it was cooled to the room temperature and extracted with 50 ml of ethyl acetate three times. After drying over magnesium sulfate, it was concentrated followed by quantifying the obtained solid by liquid chromatography.

amount: 9.16 g
purity: 93.9%
yield: 81.5%

Comparative Example 1

5.07 g (50 mmol) of a concentrated hydrochloric acid was added to 17.44 g (100 mmol) of an aqueous chloroacetaldehyde solution (45% by weight) at the room temperature. Further, an aqueous solution of 12.12 g (100 mmol)of ammonium dithiocarbamate in 12.12 g of water was dropwise added to the mixture under a water bath at the room temperature over 60 minutes. After completion of the dropwise addition, it was further stirred at the same temperature for 60 minutes. After completion of the stirring, the reaction temperature of the mixture was raised to 75° C. to complete the reaction. Then, it was cooled to the room temperature and extracted with 50 ml of ethyl acetate three times. After drying over anhydrous magnesium sulfate, it was concentrated followed by quantifying the obtained solid by liquid chromatography.

amount: 6.75 g
purity: 78.1%
yield: 45.0%

In accordance with the present invention, 2-mercaptothiazole, which is useful as an intermediate of medicines and agricultural chemicals, can be prepared, while restricting the occurrence of by-product, with a high yield.

We claim:

1. A method for preparing 2-mercaptothiazole, which comprises adding a dithiocarbamate salt represented by the formula (1):

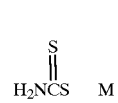

(1)

where M is a cation,
to a chloroacetaldehyde solution in the presence of an acid, and
wherein a solvent employable for said chloroacetaldehyde solution is selected from the group consisting of water, an organic solvent selected from the group consisting of methanol, ethanol, propanol, acetonitrile and tetrahydrofuran and a mixture thereof, wherein the amount of a solvent to a dithiocarbamate salt is 1–60% by weight based on total weight of the solvent used and the dithiocarbamate salt and
said acid is selected from the group consisting of hydrogen chloride, sulfuric acid, hydrogen bromide, phosphoric acid, nitric acid and p-toluenesulfonic acid and a mixture thereof, wherein the amount of said acid to be employed is 0.8–5.0 mol based on 1 mol of chloroacetaldehyde.

2. The method according to claim 1, wherein
the temperature, at which said dithiocarbamate salt is added to said chloroacetaldehyde solution in the presence of said acid, is 0° C. to about 50° C.,
the molar ratio of said dithiocarbamate salt to chloroacetaldehyde to be employed is 0.7–5.0, after the addition of said dithiocarbamate salt to said chloroacetaldehyde solution in the presence of said acid, continuing the reaction of said mixture at about 40 to about 90° C.; and the reaction time for preparing 2-mercaptothiazole is 2 to 10 hours after the addition of said dithiocarbamate salt.

3. The method according to claim 1 wherein the amount of said acid to be employed is 0.9–2.5 mol based on 1 mol of chloroacetaldehyde; and after the addition of said dithiocarbamate salt to said chloroacetaldehyde solution in the presence of said acid, the temperature at which the reaction is continued is from 50 to 80° C.

4. The method according to claim 3, wherein M is ammonium or an alkali metal.

5. The method according to claim 4, wherein said dithiocarbamate salt is ammonium dithiocarbamate and the solvent is water.

6. The method according to claim 1, wherein M is ammonium or an alkali metal.

7. The method according to claim 1, wherein said dithiocarbamate salt is ammonium dithiocarbamate.

8. The method according to claim 1, wherein said solvent employable for said chloroacetaldehyde solution is water.

9. The method according to claim 1, wherein said acid is selected from the group consisting of hydrogen chloride, sulfuric acid and the mixture thereof.

10. The method according to claim 1, wherein the amount of said acid to be employed is 0.9–2.5 mol based on 1 mol of chloroacetaldehyde.

11. The method according to claim 1, wherein the addition of said acid to said chloroacetaldehyde solution is carried out by adding said acid to said chloroacetaldehyde solution, by adding said chloroacetaldehyde solution to a solution of said acid, or by suitably adding said acid while adding said dithiocarbamate salt to said chloroacetaldehyde solution.

12. The method according to claim 1, wherein said dithiocarbamate salt is added to said acidic chloroacetaldehyde solution in the form of a solid or a solution.

13. The method according to claim 12, wherein a solvent employable in said dithiocarbamate salt solution is water.

14. The method according to claim 12, wherein, in preparation of said dithiocarbamate salt solution, the amount of a solvent to a dithiocarbamate salt is 3–55% by weight based on total weight of the solvent used and the dithiocarbamate salt.

15. The method according to claim 1, the temperature, at which said dithiocarbamate salt is added to said chloroacetaldehyde solution in the presence of said acid, is 0° C.–about 50° C.

16. The method according to claim 1, wherein the molar ratio of said dithiocarbamate salt to chloroacetaldehyde to be employed is 0.7–5.0.

17. The method according to claim 1, which further comprising, after the addition of said dithiocarbamate salt to said chloroacetaldehyde solution in the presence of said acid, continuing the reaction of said mixture at about 40–about 90° C.

18. The method according to claim 1, wherein the reaction time for preparing 2-mercaptothiazole is 2–10 hours after the addition of said dithiocarbamate salt.

* * * * *